United States Patent
Dubief et al.

(10) Patent No.: US 6,506,372 B1
(45) Date of Patent: *Jan. 14, 2003

(54) COSMETIC COMPOSITIONS CONTAINING AN AMPHOTERIC POLYMER AND A FIXING/CONDITIONER POLYMER, AND THEIR USES

(75) Inventors: Claude Dubief, Les Chesnay (FR); Serge Restle, Saint-Prix (FR)

(73) Assignee: L'Oreal S.A., Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 09/599,939

(22) Filed: Jun. 23, 2000

(30) Foreign Application Priority Data

Jun. 25, 1999 (FR) .............................. 99 08171

(51) Int. Cl.$^7$ ........................... A61K 7/00; A61K 7/06; A61K 7/08; A61K 7/075; A61K 35/36

(52) U.S. Cl. .................. 424/70.13; 424/401; 424/70.1; 424/70.6; 424/47; 514/880; 514/881; 510/123; 510/124; 510/122; 8/403; 8/404; 8/405

(58) Field of Search ............................... 424/401, 70.1, 424/70.6, 47; 514/880, 881; 8/403–405; 510/122, 123, 124

(56) References Cited

U.S. PATENT DOCUMENTS

| | | | |
|---|---|---|---|
| 2,047,398 A | 7/1936 | Voss et al. | |
| 2,261,002 A | 10/1941 | Ritter | |
| 2,271,378 A | 1/1942 | Searle | |
| 2,273,780 A | 2/1942 | Dittmar | |
| 2,375,853 A | 5/1945 | Kirby | |
| 2,388,614 A | 11/1945 | Kirby et al. | |
| 2,454,547 A | 11/1948 | Bock et al. | |
| 2,528,378 A | 10/1950 | Mannheimer | |
| 2,723,248 A | 11/1955 | Wright | |
| 2,781,354 A | 2/1957 | Mannheimer | |
| 2,961,347 A | 11/1960 | Floyd | |
| 3,206,462 A | 9/1965 | McCarty | |
| 3,227,615 A | 1/1966 | Korden | |
| 3,632,559 A | 1/1972 | Matter et al. | |
| 3,716,633 A | 2/1973 | Viout et al. | |
| 3,836,537 A | 9/1974 | Boerwinkle et al. | |
| 3,874,870 A | 4/1975 | Green et al. | |
| 3,912,808 A | 10/1975 | Sokol | |
| 3,917,817 A | 11/1975 | Vanlerberghe et al. | |

(List continued on next page.)

FOREIGN PATENT DOCUMENTS

| | | |
|---|---|---|
| DE | 90 18 158 | 1/1997 |
| EP | 0 080 976 | 6/1983 |
| EP | 0 122 324 | 10/1984 |
| EP | 0 412 704 | 2/1991 |
| EP | 0 412 707 | 2/1991 |
| EP | 0 582 152 | 2/1994 |
| EP | 0 619 111 | 10/1994 |
| EP | 0 637 600 | 2/1995 |
| EP | 0 648 485 | 4/1995 |
| EP | 0 656 021 | 6/1995 |
| EP | 0 751 162 | 1/1997 |
| EP | 0761199 B1 * | 1/1998 |
| EP | 0 887 067 | 12/1998 |
| FR | 1 222 944 | 6/1960 |
| FR | 1 400 366 | 12/1965 |
| FR | 1 492 597 | 8/1967 |
| FR | 1 564 110 | 4/1969 |
| FR | 1 580 545 | 9/1969 |
| FR | 1 583 363 | 10/1969 |

(List continued on next page.)

OTHER PUBLICATIONS

Dubuis, C, Derwent–Acc– No.: 1997–195395, Aqueous Cosmetic Composition for Spray Application to Hair . . . , Abstract.*
M.R. Porter, "Handbook of Surfactants", Blackie & Son Ltd., Glasgow & London, 1991, pp. 116–178.
English language Derwent Abstract of DE 90 18 158. (No date).
English language Derwent Abstract of EP 0 080 976. (No date).
English language Derwent Abstract of EP 0 637 600. (No date).
English language Derwent Abstract of EP 0 656 021. (No date).
English language Derwent Abstract of EP 0 751 162. (No date).
English language Derwent Abstract of FR 1 564 110. (No date).
English language Derwent Abstract of FR 2 077 143. (No date).
English language Derwent Abstract of FR 2 080 759. (No date).
English language Derwent Abstract of FR 2 320 330. (No date).
English language Derwent Abstract of FR 2 336 434. (No date).
English language Derwent Abstract of FR 2 357 241. (No date).
English language Derwent Abstract of FR 2 743 297. (No date).

Primary Examiner—Frederick Krass
Assistant Examiner—Clinton Ostrup
(74) Attorney, Agent, or Firm—Finnegan, Henderson, Farabow, Garrett & Dunner, LLP

(57) ABSTRACT

Cosmetic compositions containing in a cosmetically acceptable medium, at least one fixing and/or conditioning polymer and at least one amphoteric polymer comprising from 1 to 20 mol % of at least one monomeric unit chosen from (meth)acrylate and (meth)acrylamide types having at least one fatty chain, the fatty chain having from 8 to 30 carbon atoms. This combination may provide markedly improved cosmetic properties (disentanglement, softness) compared with the properties obtained with either of the constituents used alone. These compositions are used for washing and/or conditioning keratinous materials such as the hair or the skin.

40 Claims, No Drawings

U.S. PATENT DOCUMENTS

| | | |
|---|---|---|
| 3,929,990 A | 12/1975 | Green et al. |
| 3,966,403 A | 6/1976 | Papantoniou et al. |
| 3,966,404 A | 6/1976 | Papantoniou et al. |
| 3,966,904 A | 6/1976 | Green et al. |
| 4,001,432 A | 1/1977 | Green et al. |
| 4,005,193 A | 1/1977 | Green et al. |
| 4,013,787 A | 3/1977 | Varlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,020 A | 5/1977 | Green et al. |
| 4,031,307 A | 6/1977 | DeMartino et al. |
| 4,128,631 A | 12/1978 | Lundmark et al. |
| 4,131,576 A | 12/1978 | Lovine et al. |
| 4,137,208 A | 1/1979 | Elliott |
| 4,165,367 A | 8/1979 | Chakrabarti |
| 4,172,887 A | 10/1979 | Vanlerberghe et al. |
| 4,197,865 A | 4/1980 | Jacquet et al. |
| 4,217,914 A | 8/1980 | Jacquet et al. |
| 4,277,581 A | 7/1981 | Vanlerberghe et al. |
| 4,282,203 A | 8/1981 | Jacquet et al. |
| 4,349,532 A | 9/1982 | Vanlerberghe et al. |
| 4,591,610 A | 5/1986 | Grollier |
| 4,668,508 A | 5/1987 | Grollier et al. |
| 4,693,935 A | 9/1987 | Mazurek |
| 4,728,571 A | 3/1988 | Clemens et al. |
| 4,761,273 A | 8/1988 | Grollier et al. |
| 4,972,037 A | 11/1990 | Garbe et al. |
| 5,538,717 A | 7/1996 | La Poterie |
| 6,093,410 A * | 7/2000 | Peffly et al. ............... 424/401 |
| 6,106,577 A * | 8/2000 | Audousset et al. ............ 8/403 |

FOREIGN PATENT DOCUMENTS

| | | |
|---|---|---|
| FR | 2 077 143 | 10/1971 |
| FR | 2 080 759 | 11/1971 |
| FR | 2 162 025 | 7/1973 |
| FR | 2 190 406 | 2/1974 |
| FR | 2 252 840 | 6/1975 |
| FR | 2 265 781 | 10/1975 |
| FR | 2 265 782 | 10/1975 |
| FR | 2 270 846 | 12/1975 |
| FR | 2 280 361 | 2/1976 |
| FR | 2 361 271 | 1/1977 |
| FR | 2 320 330 | 3/1977 |
| FR | 2 336 434 | 7/1977 |
| FR | 2 350 384 | 12/1977 |
| FR | 2 357 241 | 2/1978 |
| FR | 2 368 508 | 5/1978 |
| FR | 2 393 573 | 1/1979 |
| FR | 2 413 907 | 8/1979 |
| FR | 2 439 798 | 5/1980 |
| FR | 2 505 348 | 11/1982 |
| FR | 2 542 997 | 9/1984 |
| FR | 2 743 297 | 7/1997 |
| GB | 0 839 805 | 6/1960 |
| WO | WO 93/23009 | 11/1993 |
| WO | WO 93/23446 | 11/1993 |
| WO | WO 94/03510 | 2/1994 |
| WO | WO 95/00578 | 1/1995 |
| WO | WO 98/44012 | 10/1998 |

\* cited by examiner

COSMETIC COMPOSITIONS CONTAINING AN AMPHOTERIC POLYMER AND A FIXING/CONDITIONER POLYMER, AND THEIR USES

The present invention relates to novel cosmetic compositions comprising, in a cosmetically acceptable medium, at least one fixing and/or conditioning polymer and at least one amphoteric polymer comprising from 1 to 20 mol % of at least one monomeric unit chosen from (meth)acrylate and (meth)acrylamide types having at least one fatty chain, the fatty chain having from 8 to 30 carbon atoms.

It is well known that hair which has been sensitized (i.e., damaged and/or made fragile) to various degrees under the action of atmospheric agents or under the action of mechanical or chemical treatments, such as dyeing, bleaching and/or permanent waving, is often difficult to disentangle and to style, and lacks softness.

The use of conditioning agents, in particular cationic polymers or silicones, to facilitate the disentanglement of the hair and to impart softness and suppleness to it has already been recommended in compositions for washing or caring for keratinous fibres, such as hair. However, the above-mentioned cosmetic advantages may unfortunately also be accompanied, on dried hair, by certain cosmetic effects, which are judged to be undesirable, namely an increase in the weight of the hairstyle (lack of lightness of the hair) and a lack of sleekness (hair which is not homogeneous from the root to the tip).

In addition, the use of the conditioning or fixing polymers for this purpose may have various disadvantages. Because of their high affinity for the hair, some of these polymers may become substantially deposited during repeated use, leading to undesirable effects, such as a charged, unpleasant feel, a stiffening of the hair, and an interfibre adhesion affecting hair styling. These disadvantages are accentuated in the case of fine hair, which lacks vitality and body.

In summary, it is found that the current cosmetic compositions containing fixing and/or conditioning polymers are not always completely satisfactory.

The Inventors have now discovered that the combination of an amphoteric polymer comprising fatty chains with fixing and/or conditioning polymers can allow these disadvantages to be overcome or lessened.

Thus, following major research studies carried out on subjects, it has now been found that by introducing a particular amphoteric polymer into compositions, in particular hair compositions, based on fixing or conditioning polymers, it is possible to limit, or even eliminate, the problems generally linked to the use of such compositions, such as the increase in the weight or the lack of sleekness or of softness of the hair while preserving other advantageous cosmetic properties, such as those attached to the compositions based on fixing or conditioning polymers.

This combination may provide markedly improved cosmetic properties compared with the properties obtained with either of the constituents used alone.

Moreover, the compositions of the invention, when applied to the skin, in particular in a foam bath or a shower gel form, may provide an improvement in the softness of the skin.

Thus, according to the present invention, novel cosmetic compositions are now provided, comprising, in a cosmetically acceptable medium, at least one fixing and/or conditioning polymer and at least one amphoteric polymer comprising from 1 to 20 mol % of at least one monomeric unit chosen from (meth)acrylate and (meth)acrylamide types having at least one fatty chain, the fatty chain having from 8 to 30 carbon atoms.

Another subject of the invention relates to the use of at least one amphoteric polymer comprising from 1 to 20 mol % of at least one monomeric unit chosen from (meth)acrylate and (meth)acrylamide types having at least one fatty chain, the fatty chain having from 8 to 30 carbon atoms in, or for the manufacture of a cosmetic composition comprising at least one fixing and/or conditioning polymer.

The subject of the invention is also the use of at least one amphoteric polymer comprising from 1 to 20 mol % of at least one monomeric unit chosen from (meth)acrylate and (meth)acrylamide types having at least one fatty chain, the fatty chain having from 8 to 30 carbon atoms in a composition comprising at least one fixing and/or conditioning polymer in order to increase the conditioning or fixing effect of these polymers.

The different subjects of the invention will now be presented in detail. All of the meanings and definitions of the compounds used in the present invention, which are given below, are valid for all the subjects of the invention.

The amphoteric polymers according to the invention comprise from 1 to 20 mol % of monomeric units comprising a fatty chain, and preferably from 1.5 to 15 mol %, and still more preferably from 1.5 to 6 mol % relative to the total number of moles of monomeric units in the polymers.

The amphoteric polymers according to the invention may result from the copolymerization 1) of at least one monomer chosen from (meth)acrylate and (meth)acrylamide types of formula (Ia) and (Ib):

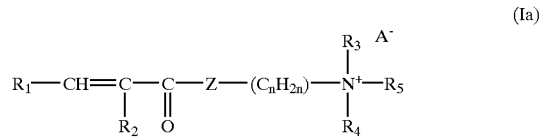

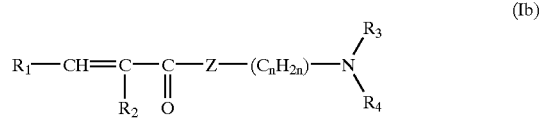

in which: $R_1$ and $R_2$, which are identical or different, are a hydrogen atom or a methyl radical; $R_3$, $R_4$ and $R_5$, which are identical or different, are chosen from linear and branched alkyl radicals having from 1 to 30 carbon atoms;

Z is an NH group or an oxygen atom;

n is an integer ranging from 2 to 5; and $A^-$ is an anion derived from an organic or inorganic acid, such as a methosulphate anion or a halide, such as chloride or bromide, 2) of at least one monomer chosen from (meth)acrylate and (meth)acrylamide types of formula (II)

$$R_6\text{---}CH\text{=}CR_7\text{---}COOH \quad (II)$$

in which: $R_6$ and $R_7$, which are identical or different, are a hydrogen atom or a methyl radical;

and 3) of at least one monomer chosen from (meth)acrylate and (meth)acrylamide types of formula (III):

$$R_6\text{---}CH\text{=}CR_7\text{---}COXR_8 \quad (III)$$

in which: $R_6$ and $R_7$, which are identical or different, are a hydrogen atom or a methyl radical; X is an oxygen or nitrogen atom; and $R_8$ is chosen from linear and branched alkyl radicals having from 1 to 30 carbon atoms;

at least one of the (meth)acrylate and (meth)acrylamide type monomers of formula (Ia), (Ib) or (III) comprises at least one fatty chain having from 8 to 30 carbon atoms.

The monomers of formula (Ia) and (Ib) of the present invention are preferably chosen from:

dimethylaminoethyl methacrylate, dimethylaminoethyl acrylate, diethylaminoethyl methacrylate, diethylaminoethyl acrylate, dimethylaminopropyl methacrylate, dimethylaminopropyl acrylate, and dimethylaminopropylmethacrylamide, dimethylaminopropylacrylamide, these monomers being optionally quaternized, for example, with a ($C_1$–$C_4$) alkyl halide or a ($C_1$–$C_4$) dialkyl sulphate.

More particularly, the monomer of formula (Ia) is chosen from acrylamidopropyltrimethylammonium chloride and methacrylamidopropyltrimethylammonium chloride.

The monomers of formula (II) of the present invention are preferably chosen from acrylic acid, methacrylic acid, crotonic acid and 2-methylcrotonic acid.

More particularly, the monomer of formula (II) is acrylic acid.

The monomers of formula (III) of the present invention are preferably chosen from ($C_{12}$–$C_{22}$), and more particularly ($C_{16}$–$C_{18}$), alkyl acrylates and methacrylates.

The monomeric units constituting the amphoteric polymers of the invention are preferably already neutralized and/or quaternized.

The ratio of the number of cationic charges/anionic charges is preferably equal to about 1.

The weight-average molecular weights of the amphoteric polymers according to the invention can range from 500 to 50,000,000 and are preferably from 10,000 to 5,000,000.

Polymers according to the invention can also contain other monomers, such as nonionic monomers and in particular such as ($C_1$–$C_4$) alkyl acrylates or methacrylates.

Amphoteric polymers according to the invention are in particular described in patent application WO 98/44012, the disclosure of which is incorporated by reference.

The particularly preferred amphoteric polymers according to the invention are chosen from acrylic acid/acrylamidopropyltrimethylammonium chloride/stearyl methacrylate copolymers.

The amphoteric polymer is generally used in the composition in an amount ranging from 0.05 to 10% by weight relative to the total weight of the composition. Preferably, this amount ranges from 0.1 to 5% by weight relative to the total weight of the composition.

Fixing polymer is understood to mean any polymer whose function is to temporarily fix the shape of the hairstyle.

In the context of the present application, conditioning polymer is understood to mean any polymer whose function is to improve the cosmetic properties of the hair, in particular the softness, disentanglement, feel and static electricity.

According to the invention, it is possible to use any fixing and/or conditioning polymer known per se. It is possible to use in particular a fixing and/or conditioning polymer chosen from the anionic, cationic, amphoteric and nonionic polymers and mixtures thereof.

The conditioning polymers are preferably chosen from cationic and amphoteric polymers and mixtures thereof.

The fixing and/or conditioning polymers may be used in a solubilized form or in the form of a latex (aqueous dispersion of solid particles of polymer).

The anionic film-forming polymers generally used are polymers containing groups derived from carboxylic, sulphonic or phosphoric acid and have a weight average molecular weight ranging from about 500 to 5,000,000.

1) The carboxylic groups are provided by unsaturated mono- or dicarboxylic acid monomers such as those corresponding to the formula (IX):

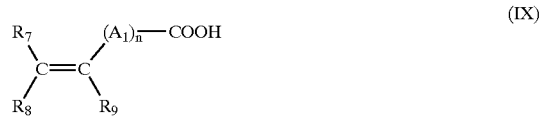

in which: n is an integer ranging from 0 to 10; $A_1$ is a methylene group, optionally linked to the carbon atom of the unsaturated group or to the neighboring methylene group, when n is greater than 1, through a heteroatom such as oxygen or sulphur; $R_7$ is chosen from a hydrogen atom, a phenyl group, and a benzyl group; $R_8$ is chosen from a hydrogen atom, a carboxyl group, and a lower alkyl group, $R_9$ is chosen from a hydrogen atom, a lower alkyl group, a —$CH_2$—COOH group, a phenyl group, and a benzyl group.

In the above-mentioned formula (IX), a lower alkyl radical is preferably a group having from 1 to 4 carbon atoms, and is in particular a methyl or ethyl group.

The anionic film-forming polymers with carboxylic groups preferred according to the invention are:

A) homo- or copolymers of acrylic or methacrylic acid or their salts and in particular the products sold under the names VERSICOL E or K by the company ALLIED COLLOID and ULTRAHOLD by the company BASF. The copolymers of acrylic acid and of acrylamide sold in the form of their sodium salt under the names RETEN 421, 423 or 425 by the company HERCULES, and the sodium salts of the polyhydroxycarboxylic acids;

B) copolymers of acrylic or methacrylic acids with a monoethylene monomer, such as ethylene, styrene, vinyl esters, acrylic or methacrylic acid esters, optionally grafted onto a polyalkylene glycol, such as polyethylene glycol and optionally crosslinked. Such polymers are described in particular in French Patent 1,222,944 and German Application 2,330,956, the disclosures of which are incorporated by reference. Copolymers of this type containing in their chain an acrylamide unit optionally N-alkylated and/or hydroxyalkylated are described especially in Luxembourg Patent applications 75370 and 75371, the disclosures of which are incorporated by reference, or offered under the name QUADRAMER by the company AMERICAN CYANAMID. There may also be mentioned the copolymers of acrylic acid and ($C_1$–$C_4$) alkyl methacrylate and the terpolymers of vinylpyrrolidone, acrylic acid and ($C_1$–$C_{20}$) alkyl, for example lauryl, methacrylate such as that sold by the company ISP under the name ACRYLIDONE LM and the methacrylic acid/ethyl acrylate/tert-butyl acrylate terpolymers such as the product sold under the name LUVIMER 100 P by the company BASF;

C) copolymers derived from crotonic acid, such as those containing in their chain vinyl propionate or acetate units and optionally other monomers, such as methallyl or allyl esters, vinyl ether or vinyl ester of a linear or branched saturated carboxylic acid with a long hydrocarbon chain, such as those containing at least 5 carbon atoms. It being possible for these polymers to be optionally grafted and crosslinked or alternatively a vinyl, allyl or methallyl ester of an - or β-cyclic carboxylic acid. Such polymers are described, inter alia, in French Patents 1,222,944; 1,580,545; 2,265, 782; 2,265,781; 1,564,110 and 2,439,798, the disclosures of which are incorporated by reference. Commercial products entering into this class are the resins 28-29-30, 26-13-14 and 28-13-10 sold by the company NATIONAL STARCH;

D) copolymers derived from ($C_4$–$C_8$) monounsaturated carboxylic acids or anhydrides chosen from:

copolymers comprising (i) at least one acidic unit chosen from itaconic acid, fumaric acid, maleic acid and anhydrides thereof and (ii) at least one monomeric unit chosen from vinyl esters, vinyl ethers, vinyl halides, phenylvinyl derivatives, acrylic acid and its esters. The anhydride functions of these copolymers are optionally monoesterified or monoamidated. Such polymers are described in particular in U.S. Pat. Nos. 2,047,398; 2,723,248; and 2,102, 113; Great Britain Patent GB 839,805, the disclosures of which are incorporated by reference, and especially those sold under the names GANTREZ AN or ES by the company ISP, and copolymers comprising (i) at least one anhydride unit chosen from maleic, citraconic and itaconic anhydrides and (ii) at least one monomeric unit chosen from allyl and methallyl esters optionally containing one at least one group chosen from acrylamide, methacrylamide, -olefins, acrylic esters, methacrylic esters, acrylic acid, methacrylic acid and vinylpyrrolidone groups in their chain. The anhydride functions of these copolymers are optionally monoesterified or monoamidated.

These polymers are, for example, described in French Patents 2,350,384 and 2,357,241, assigned to L'Oréal, the disclosures of which are incorporated by reference.

E) polyacrylamides containing carboxylate groups.

The polymers comprising sulphonic groups are polymers containing vinylsulphonic, styrenesulphonic, naphthalenesulphonic or acrylamidoalkylsulphonic units.

These polymers may be chosen from:

salts of polyvinylsulphonic acid having a molecular weight ranging from about 1000 to 100,000 as well as the copolymers with an unsaturated comonomer, such as acrylic or methacrylic acids and their esters as well as acrylamide or its derivatives, vinyl ethers and vinylpyrrolidone;

salts of polystyrenesulphonic acid. The sodium salts have a molecular weight ranging from about 500,000 to 100,000, sold respectively under the names FLEXAN 500 and FLEXAN 130 by National Starch. These compounds are described in French Patent 2,198,719, the disclosure of which is incorporated by reference; and salts of polyacrylamidesulphonic acids, such as those mentioned in U.S. Pat. No. 4,128,631, the disclosure of which is incorporated by reference, and more particularly polyacrylamidoethylpropanesulphonic acid sold under the name COSMEDIA POLYMER HSP 1180 by Henkel.

According to the invention, the anionic film-forming polymers are preferably chosen from acrylic acid copolymers, such as the terpolymer acrylic acid/ethyl acrylate/N-tert-butylacrylamide sold under the name ULTRAHOLD STRONG by the company BASF, the copolymers derived from crotonic acid, such as the terpolymers vinyl acetate/vinyl tert-butylbenzoate/crotonic acid and the terpolymers crotonic acid/vinyl acetate/vinyl neododecanoate sold under the name RÉSINE 28-29-30 by the company NATIONAL STARCH, the polymers derived from itaconic, fumaric and maleic acids or anhydrides with vinyl esters, vinyl ethers, vinyl halides, phenylvinyl derivatives, acrylic acid and its esters, such as the monoesterified maleic anhydride/methylvinyl ether copolymer sold under the name GANTREZ ES 425 by the company ISP, the copolymers of methacrylic acid and of methyl methacrylate sold under the name EUDRAGIT L by the company ROHM PHARMA, the copolymer of methacrylic acid and of ethyl acrylate sold under the name LUVIMER MAEX or MAE by the company BASF and the copolymer vinyl acetate/crotonic acid sold under the name LUVISET CA 66 by the company BASF, and the copolymer vinyl acetate/crotonic acid grafted with polyethylene glycol under the name ARISTOFLEX A by the company BASF.

The anionic film-forming polymers most particularly preferred are those chosen from monoesterified maleic anhydride/methylvinyl ether copolymer sold under the name GANTREZ ES 425 by the company ISP, the terpolymer acrylic acid/ethyl acrylate/N-tert-butylacrylamide sold under the name ULTRAHOLD STRONG by the company BASF, the copolymers of methacrylic acid and of methyl methacrylate sold under the name EUDRAGIT L by the company ROHM PHARMA, the terpolymers vinyl acetate/ vinyl tert-butylbenzoate/crotonic acid and the terpolymers crotonic acid/vinyl acetate/vinyl neododecanoate sold under the name RÉSINE 28-29-30 by the company NATIONAL STARCH, the copolymer of methacrylic acid and ethyl acrylate sold under the name LUVIMER MAEX or MAE by the company BASF, the terpolymer vinylpyrrolidone/acrylic acid/lauryl methacrylate sold under the name ACRYLIDONE LM by the company ISP.

Still more generally, for the purposes of the present invention, the expression "cationic polymer" is any polymer containing cationic groups and/or groups ionizable into cationic groups.

The preferred cationic polymers are chosen from those which contain units comprising primary, secondary, tertiary and/or quaternary amine groups, which may either form part of the principal polymer chain, or which may be carried by a side substituent directly linked thereto.

The cationic polymers used generally have a number-average molecular mass ranging from 500 to $5 \times 10^6$ approximately, and preferably ranging from 1000 to $3 \times 10^6$ approximately.

Among the cationic polymers, there may be mentioned more particularly the polymers of the polyamine, polyaminoamide and quaternary polyammonium type. They are known products.

The polymers of the polyamine, polyaminoamide and quaternary polyammonium type which can be used in accordance with the present invention, which may be especially mentioned, are those described in French Patents No. 2,505, 348 or 2,542,997, the disclosures of which are incorporated by reference. Among these polymers, there may be mentioned:

(1) the homopolymers or copolymers derived from acrylic or methacrylic esters or amides and comprising at least one of unit of the following formulae:

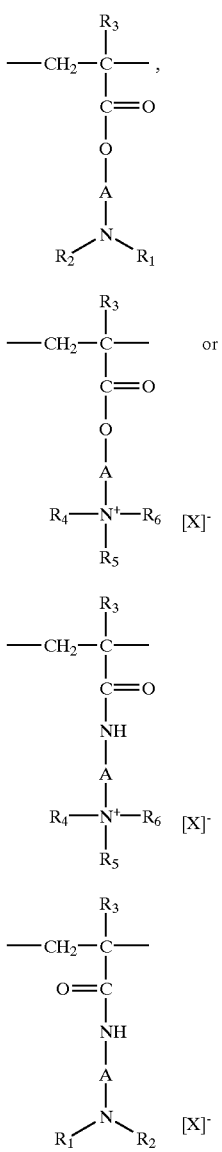

in which:
- $R_3$, which are identical or different, is chosen from a hydrogen atom and a $CH_3$ radical; A, which are identical or different, is chosen from a hydroxyalkyl group having from 1 to 4 carbon atoms, a linear and branched alkyl group having from 1 to 6 carbon atoms, preferably 2 or 3 carbon atoms;
- $R_4$, $R_5$, $R_6$, which are identical or different, are chosen from an alkyl group having from 1 to 18 carbon atoms and a benzyl radical, and preferably an alkyl group having from 1 to 6 carbon atoms;
- $R_1$, and $R_2$, which are identical or different, are chosen from a hydrogen atom, an alkyl group having from 1 to 6 carbon atoms, and preferably methyl or ethyl; and
- X is an anion derived from an inorganic or organic acid, such as a methosulphate anion or a halide, such as chloride or bromide.

The copolymers of the family (1) may contain, in addition, at least one unit derived from comonomers which may be chosen from acrylamides, methacrylamides, diacetone acrylamides, acrylamides and methacrylamides substituted on the nitrogen with lower ($C_1$–$C_4$)alkyls, acrylic acids, methacrylic acids and esters thereof, and vinyllactams, such as vinylpyrrolidone or vinylcaprolactam, vinyl esters.

Thus, among these copolymers of the family (1), there may be mentioned:
- copolymers of acrylamide and dimethylamino-ethyl methacrylate quaternized with dimethyl sulphate or with dimethyl halide, such as that sold under the name HERCOFLOC by the company HERCULES,
- copolymers of acrylamide and methacryloyloxyethyltrimethylammonium chloride described, for example, in Patent Application EP-A-080976, the disclosure of which is incorporated by reference, and sold under the name BINA QUAT P 100 by the company CIBA GEIGY,
- a copolymer of acrylamide and methacryloyloxyethyltrimethylammonium methosulphate sold under the name RETEN by the company HERCULES,
- vinylpyrrolidone/dialkylaminoalkyl acrylate or methacrylate copolymers, quaternized or otherwise, such as the products sold under the name GAFQUAT by the company ISP, such as for example GAFQUAT 734 or GAFQUAT 755 or alternatively the products called COPOLYMER 845, 958 and 937. These polymers are described in detail in French Patents 2,077,143 and 2,393,573, the disclosures of which are incorporated by reference,
- dimethylaminoethyl methacrylate/vinylcapro-lactam/ vinylpyrrolidone terpolymers such as the product sold under the name GAFFIX VC 713 by the company ISP,
- vinylpyrrolidone/methacrylamidopropyldimethyl-amine copolymers marketed in particular under the name STYLEZE CC 10 by ISP, and
- quaternized vinylpyrrolidone/dimethyl-aminopropyl methacrylamide copolymers such as the product sold under the name GAFQUAT HS 100 by the company ISP.

(2) The cellulose ether derivatives comprising quaternary ammonium groups, described in French Patent 1,492,597, the disclosure of which is incorporated by reference, and in particular the polymers marketed under the names JR (JR 400, JR 125, JR 30M) or LR (LR 400, LR 30M) by the company Union Carbide Corporation. These polymers are also defined in the CTFA dictionary as hydroxyethyl cellulose quaternary ammoniums which have reacted with an epoxide substituted by a trimethylammonium group.

(3) Cationic cellulose derivatives, such as cellulose copolymers or cellulose derivatives grafted with a quaternary ammonium water-soluble monomer, and described especially in U.S. Pat. No. 4,131,576, the disclosure of which is incorporated by reference, such as hydroxyalkyl celluloses like hydroxymethyl, hydroxyethyl or hydroxypropyl celluloses grafted with a methacryloylethyltrimethylammonium, methacrylamidopropyltrimethylammonium or dimethyidiallylammonium salt.

The commercialized products corresponding to this definition are more particularly the products sold under the name CELQUAT L 200 and CELQUAT H 100 by the company National Starch.

(4) The cationic polysaccharides described more particularly in U.S. Pat. Nos. 3,589,578 and 4,031,307, the disclosures of which are incorporated by reference, such as guar gums containing cationic trialkylammonium groups. Guar gums modified with a 2,3-epoxypropyltri-methylammonium salt (e.g., chloride) are for example used.

Such products are marketed in particular under the trade names JAGUAR C13 S, JAGUAR C 15, JAGUAR C 17 or JAGUAR C162 by the company MEYHALL.

(5) Polymers comprising piperazinyl units and alkylene or hydroxyalkylene divalent radicals with straight or branched chains, optionally interrupted by oxygen, sulphur or nitrogen atoms or by aromatic or heterocyclic rings, as well as the oxidation and/or quaternization products of these polymers. Such polymers are described especially in French patents 2,162,025 and 2,280,361, the disclosures of which are incorporated by reference;

(6) Water-soluble polyaminoamides prepared in particular by polycondensation of an acid compound with a polyamine. These polyaminoamides may be crosslinked with an epihalohydrin, a diepoxide, a dianhydride, an unsaturated dianhydride, a diunsaturated derivative, a bishalohydrin, a bisazetidinium, a bishaloacyidiamine, an alkylbishalide or else with an oligomer resulting from the reaction of a difunctional compound, which is reactive towards a bishalohydrin, a bisazetidinium, a bishaloacyldiamine, an alkylbishalide, an epihalohydrin, a diepoxide or a diunsaturated derivative. The crosslinking agent is employed in proportions ranging from 0.025 to 0.35 mol per amine group of the polyaminoamide. These polyaminoamides may be alkylated or, if they include one or more tertiary amine functional groups, quaternized. Such polymers are described especially in French Patents 2,252,840 and 2,368,508, the disclosures of which are incorporated by reference;

(7) Polyaminoamide derivatives resulting from the condensation of polyalkylenepolyamines with polycarboxylic acids, followed by an alkylation with difunctional agents. There may be mentioned, for example, the adipic acid—dialkylaminohydroxyalkyldialkylenetriamine polymers in which the alkyl radical contains from 1 to 4 carbon atoms and preferably is methyl, ethyl or propyl. Such polymers are described especially in French Patent 1,583,363, the disclosure of which is hereby incorporated by reference.

Among these derivatives there may be mentioned more particularly the adipic acid/dimethyl-aminohydroxypropyl/diethylenetriamine polymers sold under the name CARTARETINE F, F4 or F8 by the compnay Sandoz.

(8) Polymers obtained by reaction of a polyalkylenepolyamine containing two primary amine groups and at least one secondary amine group with a dicarboxylic acid chosen from diglycolic acid and saturated aliphatic dicarboxylic acids containing from 3 to 8 carbon atoms. The molar ratio of the polyalkylenepolyamine to the dicarboxylic acid is from 0.8:1 to 1.4:1. The polyaminoamide resulting therefrom is made to react with epichlorohydrin in a molar ratio of epichlorohydrin relative to the secondary amine group of the polyaminoamide of from 0.5:1 to 1.8:1. Such polymers are described especially in U.S. Pat. Nos. 3,227,615 and 2,961,347, the disclosures of which are incorporated by reference.

Polymers of this type are marketed in particular under the name HERCOSETT 57 by the company Hercules Inc. or else under the name of PD 170 or DELSETTE 101 by the company Hercules in the case of the copolymer of adipic acid/epoxypropyl/diethyl-triamine.

(9) Cyclohomopolymers of alkyldiallylamine or of dialkyldiallylammonium, such as the homopolymers or copolymers comprising, as a main constituent of the chain, units corresponding to the formulae (VI) or (VI'):

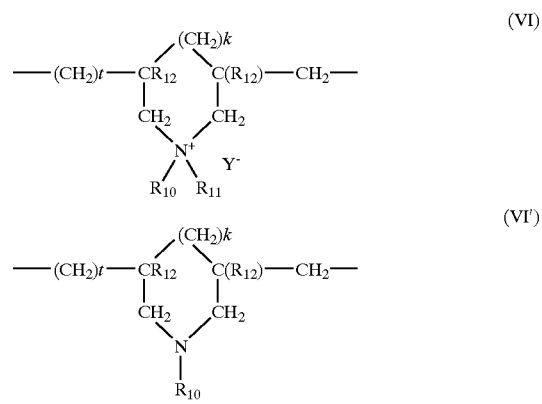

in which formulae: k and t, independently of each other, are equal to 0 or 1, the sum k+t being equal to 1; $R_{12}$ is chosen from a hydrogen atom and a methyl radical; $R_{10}$ and $R_{11}$, independently of each other, are chosen from an alkyl group containing from 1 to 22 carbon atoms, a hydroxyalkyl group in which the alkyl group preferably has 1 to 5 carbon atoms, and a lower ($C_1$–$C_4$)amidoalkyl group, or $R_{10}$ and $R_{11}$ may be, jointly with the nitrogen atom to which they are attached, heterocyclic groups such as piperidinyl or morpholinyl; Y is an anion, such as bromide, chloride, acetate, borate, citrate, tartrate, bisulphate, bisulphite, sulphate or phosphate. These polymers are described especially in French Patent 2,080,759 and in its certificate of addition 2,190,406, the disclosures of which are incorporated by reference.

$R_{10}$ and $R_{11}$, independently of each other, preferably are an alkyl group having from 1 to 4 carbon atoms.

Among the polymers defined above there may be mentioned more particularly the dimethyldiallylammonium chloride homopolymer sold under the name MERQUAT 100 by the company Calgon (and its homologues of low weight-average molecular masses) and the copolymers of diallyldimethylammonium chloride and acrylamide marketed under the name MERQUAT 550.

(10) The quaternary diammonium polymer containing repeat units corresponding to the formula (VII):

in which:

$R_{13}$, $R_{14}$, $R_{15}$ and $R_{16}$, which are identical or different, are chosen from aliphatic radicals containing from 1 to 20 carbon atoms, alicyclic radicals containing from 4 to 20 carbon atoms, arylaliphatic radicals containing from 7 to 20 carbon atoms, and lower hydroxyalkyl aliphatic radicals, or else $R_{13}$, $R_{14}$, $R_{15}$ and $R_{16}$, together or separately, form, with the nitrogen atoms to which they are attached, heterocyclic rings optionally containing a second heteroatom other than nitrogen, or else $R_{13}$, $R_{14}$, $R_{15}$ and $R_{16}$ are chosen from linear and branched ($C_1$–$C_6$) alkyl radicals substituted by a nitrile, ester, acyl, amide, a —CO—O—$R_{17}$—D group, or a —CO—NH—$R_{17}$—D group where $R_{17}$ is an alkylene and D is a quaternary ammonium group;

$A_1$ and $B_1$, which are identical or different, are chosen from polymethylene groups containing from 2 to 20 carbon atoms, which may be linear or branched, saturated or unsaturated and, which may contain, bonded to or inserted into the main chain, one or several aromatic rings, at least one oxygen atom, sulphur atom, and sulphoxide, sulphone, disulphide, amino, alkylamino, hydroxyl, quaternary ammonium, ureido, amide or ester groups, and $X^-$ is an anion derived from an inorganic or organic acid.

$A_1$, $R_{13}$ and $R_{15}$, with the two nitrogen atoms to which they are attached, may form a piperazine ring. In addition if $A_1$ is a saturated or unsaturated, linear or branched alkylene or hydroxyalkylene radical, $B_1$ may also be a group $(CH_2)_n$—CO—D—OC—$(CH_2)_n$—
wherein n is an integer from 1 to 6, in which D is:
 a) a glycol residue of formula: —O—Z—O—, where Z is chosen from a linear hydrocarbon radical, a branched hydrocarbon radical, and a group corresponding to one of the following formulae:

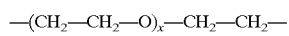

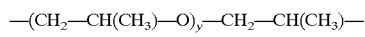

where x and y, which are identical or different, are integers ranging from 1 to 4, representing a defined and unique degree of polymerization or any number from 1 to 4 representing a mean degree of polymerization;
 b) a disecondary diamine residue, such as a piperazine derivative;
 c) a diprimary diamine residue of formula: —NH—Y—NH—, where Y is chosen from a linear hydrocarbon radical, a branched hydrocarbon radical, and the divalent radical

d) a ureylene group of formula: —NH—CO—NH—.

$X^-$ is preferably an anion, such as chloride or bromide.

These polymers have a number-average molecular mass which is generally from 1000 to 100,000.

Polymers of this type are described especially in French Patents 2,320,330, 2,270,846, 2,316,271, 2,336,434 and 2,413,907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020, the disclosures of which are incorporated by reference.

It is possible to use more particularly the polymers which comprise repeat units corresponding to the formula:

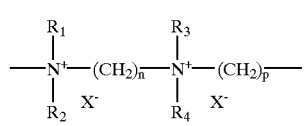

(a)

in which: $R_1$, $R_2$, $R_3$ and $R_4$, which are identical or different, are chosen from an alkyl radical having from 1 to 4 carbon atoms and a hydroxyalkyl having from 1 to 4 carbon atoms approximately; n and p are integers ranging from 2 to 20 approximately; and $X^-$ is an anion derived from an inorganic or organic acid.

A preferred compound of formula (a) is that for which $R_1$, $R_2$, $R_3$ and $R_4$ are a methyl radical, n=3, p=6, and X=Cl, called Hexadimethrine chloride according to the INCI nomenclature (CTFA).

(11) quaternary polyammonium polymers comprising units of formula (VIII):

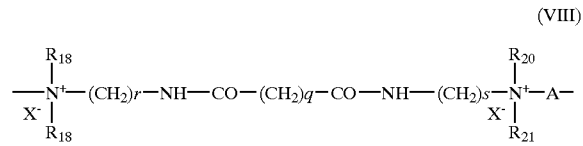

(VIII)

in which:
 $R_{18}$, $R_{19}$, $R_{20}$ and $R_{21}$, which are identical or different, are chosen from a hydrogen atom, a methyl radical, an ethyl radical, a propyl radical, a $\beta$-hydroxyethyl radical, a $\beta$-hydroxypropyl radical, and a —$CH_2CH_2$ $(OCH_2CH_2)_p$OH radical,
 where p is equal to 0 or to an integer ranging from 1 to 6, provided that $R_{18}$, $R_{19}$, $R_{20}$ and $R_{21}$ are not simultaneously a hydrogen atom,
 r and s, which are identical or different, are integers ranging from 1 to 6,
 q is equal to 0 or to an integer ranging from 1 to 34,
 X is a halogen atom,
 A is a radical of a dihalide or preferably represents —$CH_2$—$CH_2$—O—$CH_2$—$CH_2$—.

Such compounds are described especially in Patent Application EP-A-1 22 324, the disclosure of which is incorporated by reference.

Among these there may be mentioned, for example, the products MIRAPOL A 15, MIRAPOL AD1, MIRAPOL AZ1 and MIRAPOL 175, sold by the company Miranol.

(12) Quaternary vinylpyrrolidone and vinylimidazole polymers such as, for example, the products marketed under the names LUVIQUAT FC 905, FC 550 and FC 370 by the company B.A.S.F.

(13) Polyamines like POLYQUART H sold by Henkel, referred to under the name of "Polyethylene glycol (15) Tallow Polyamine" in the CTFA dictionary.

(14) The crosslinked polymers of methacryloyloxy($C_1$–$C_4$ alkyl)tri($C_1$–$C_4$ alkyl)ammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride. The homo- or copolymerization being followed by crosslinking with a compound containing olefinic unsaturation, in particular methylenebisacrylamide. More particularly, it is possible to employ a crosslinked acrylamide/methacryloyloxyethyltrimethylammonium chloride copolymer (20/80 by weight) in the form of a dispersion containing 50% by weight of the copolymer in mineral oil. This dispersion is marketed under the name of SALCARE® SC 92 by the company Allied Colloids. It is also possible to employ a crosslinked methacryloyloxyethyltrimethylammonium chloride homopolymer containing approximately 50% by weight of the homopolymer in mineral oil or in a liquid ester. These dispersions are marketed under the names of SALCARE® SC 95 and SALCARE® SC 96 by the company Allied Colloids.

Other cationic polymers that may be employed within the scope of the invention are cationic proteins or hydrolysates of cationic proteins, polyalkyleneimines, in particular polyethyleneimines, polymers containing vinylpyridine or vinylpyridinium units, condensates of polyamines and of epichlorohydrin, quaternary polyureylenes and chitin derivatives.

Among all the cationic polymers capable of being used within the scope of the present invention, it is preferable to use quaternary cellulose ether derivatives such as the products sold under the name JR 400 by the company UNION CARBIDE CORPORATION, cyclopolymers, in particular the polymers or copolymers of dimethyl-diallylammonium chloride and of acrylamide, sold under the names MERQUAT 100, MERQUAT 550 and MERQUAT S by the company CALGON, cationic polysaccharides, such as guar gums modified by 2,3-epoxypropyltrimethylammonium chloride which are marketed, for example, under the name JAQUAR C13S by the company MEYHALL and the vinylpyrrolidone/methacrylamidopropyldimethylamine copolymers marketed in particular under the name STYLEZE CC 10 by the company ISP and mixtures thereof.

The film-forming amphoteric polymers which can be used in accordance with the invention may be chosen from the polymers containing B and C units distributed statistically in the polymer chain where B is a unit which is derived from a monomer containing at least one basic nitrogen atom and C is a unit which is derived from an acidic monomer containing at least one carboxylic or sulphonic groups or alternatively B and C may be groups which are derived from zwitterionic monomers of carboxybetaines or of sulphobeta B and C may also be a cationic polymer chain containing primary, secondary, tertiary or quaternary amine groups, in which at least one of the amine groups carries a carboxylic or sulphonic group linked via a hydrocarbon radical. Alternatively B and C can form part of a chain of a polymer with an ,β-dicarboxylic ethylene unit in which one of the carboxylic groups has been caused to react with a polyamine containing one or more primary or secondary amine groups.

The amphoteric film-forming polymers corresponding to the definition given above which are more particularly preferred are chosen from the following polymers:

1) The polymers resulting from the copolymerization of a monomeric unit derived from a vinyl compound carrying a carboxylic group, such as more particularly acrylic acid, methacrylic acid, maleic acid, alpha-chloroacrylic acid, and of a basic monomeric unit derived from a substituted vinyl compound containing at least one basic atom, such as more particularly dialkylaminoalkyl methacrylate and acrylate, dialkylaminoalkylmethacrylamide and acrylamide. Such compounds are described in U.S. Pat. No. 3,836,537, the disclosure of which is incorporated by reference.

(2) The polymers containing units which are derived from:
   a) at least one monomer chosen from acrylamides and methacrylamides substituted on the nitrogen by an alkyl radical,
   b) at least one acidic comonomer containing one or more reactive carboxylic groups, and
   c) at least one basic comonomer, such as esters with primary, secondary, tertiary and quaternary amine substituents of acrylic and methacrylic acids and the product of quaternization of dimethylaminoethyl methacrylate with dimethyl or diethyl sulphate.

The N-substituted acrylamides or methacrylamides most particularly preferred according to the invention are groups whose alkyl radicals contain from 2 to 12 carbon atoms and more particularly N-ethylacrylamide, N-tert-butylacrylamide, N-tert-octylacrylamide, N-octylacrylamide, N-decylacrylamide, N-dodecylacrylamide as well as the corresponding methacrylamides.

The acidic comonomers are chosen more particularly from acrylic, methacrylic, crotonic, itaconic, maleic and fumaric acids as well as the alkyl monoesters having 1 to 4 carbon atoms of maleic or fumaric anhydrides or acids.

The basic comonomers preferred are methacrylates of aminoethyl, butylaminoethyl, N,N'-dimethylaminoethyl, and N-tert-butylaminoethyl.

Particularly used are the copolymers whose CTFA name (4th ed. 1991), the disclosure of which is incorporated by reference, is Octylacrylamide/acrylates/butylaminoethylmethacrylate copolymer such as the products sold under the name AMPHOMER or LOVOCRYL 47 by the company NATIONAL STARCH.

(3) The partially or completely alkylated and crosslinked polyaminoamides derived from polyaminoamides of general formula (IVa):

(IVa)

in which: $R_{10}$ is chosen from a divalent radical derived from a saturated dicarboxylic acid, a mono- or dicarboxylic aliphatic acid with ethylenic double bond, an ester of a lower alkanol having 1 to 6 carbon atoms of these acids, and a radical which is derived from the addition of any one of the acids with a bis-primary or bis-secondary amine, and Z is a radical of a bis-primary, mono- or bis-secondary polyalkylene-polyamine and preferably is:

a) in the proportions of 60 to 100 mol %, the radical (IVb):

(IVb)

where x=2 and p=2 or 3, or alternatively x=3 and p=2, this radical being derived from diethylenetriamine, triethylenetetraamine or dipropylenetriamine;

b) in the proportions of 0 to 40 mol %,the radical (IVb) above, in which x=2 and p=1 and which is derived from ethylenediamine, or the radical which is derived from piperazine:

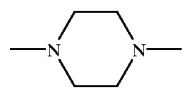

c) in the proportions of 0 to 20 mol %, the radical —NH—$(CH_2)_6$—NH— which is derived from hexamethylenediamine. These polyamino amines being crosslinked by adding a bifunctional crosslinking agent chosen from epihalohydrins, diepoxides, dianhydrides, bis-unsaturated derivatives, by means of 0.025 to 0.35 mol of crosslinking agent per amine group of the polyamino amide and alkylated by the action of acrylic acid, chloroacetic acid or of an alkanesultone or of their salts.

The saturated carboxylic acids are preferably chosen from acids having from 6 to 10 carbon atoms, such as adipic, 2,2,4-trimethyladipic and 2,4,4-trimethyladipic acid, terephthalic acid, and acids with ethylene double bond such as for example acrylic, methacrylic and itaconic acids.

The alkanesultones used in the alkylation are preferably propane or butanesultone. The salts of the alkylating agents are preferably the sodium or potassium salts.

4) The polymers containing zwitterionic units of formula (V):

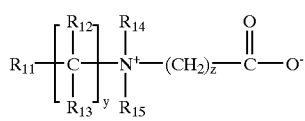
(V)

in which: $R_{11}$ is a polymerizable unsaturated group, such as an acrylate, methacrylate, acrylamide or methacrylamide group; y and z, which are identical or different, are an integer ranging from 1 to 3; $R_{12}$ and $R_{13}$, which are identical or different, are chosen from a hydrogen atom, methyl, ethyl, and propyl; $R_{14}$ and $R_{15}$, which are identical or different, are a hydrogen atom or an alkyl radical, such that the sum of the carbon atoms in $R_{14}$ and $R_{15}$ does not exceed 10.

The polymers comprising such units may also comprise units derived from nonzwitterionic monomers, such as dimethyl or diethylaminoethyl acrylate or methacrylate or alkyl acrylates or methacrylates, acrylamides or methacrylamides or vinyl acetate.

By way of example, there may be mentioned the copolymer of methyl methacrylate/methyl dimethylcarboxymethylammonioethyl methacrylate, such as the product sold under the name DIAFORMER Z301 by the company SANDOZ.

(5) The polymers derived from chitosan containing monomeric units corresponding to the following formulae (E, F, G):

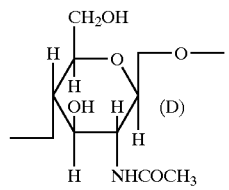
(E)

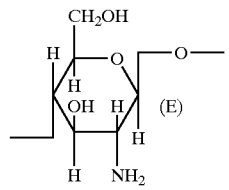
(F)

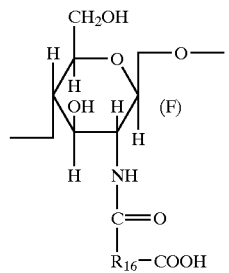
(G)

the E unit being present in proportions ranging from 0 to 30%, the F unit being present in proportions ranging from 5 to 50%, and the G unit being present in proportions ranging from 30 to 90%, it being understood that in the G unit, $R_{16}$ is a radical of formula (X):

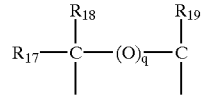
(X)

in which: if q=0, $R_{17}$, $R_{18}$ and $R_{19}$, which are identical or different, are chosen from a hydrogen atom, a methyl residue, a hydroxyl residue, an acetoxy residue, an amino residue, a monoalkylamine residue, and a dialkylamine residue optionally interrupted by at least one nitrogen atom and/or optionally substituted with at least one amine, hydroxyl, carboxyl, alkylthio or sulphonic group, and an alkylthio residue whose alkyl group carries an amino residue, at least one of the $R_{17}$, $R_{18}$ and $R_{19}$ radicals being in this case a hydrogen atom;

or if q=1, $R_{17}$, $R_{18}$ and $R_{19}$ each are a hydrogen atom, as well as the salts formed by these compounds with bases or acids.

(6) The polymers derived from the N-carboxyalkylation of chitosan, such as N-carboxymethyl chitosan or N-carboxybutyl chitosan sold under the name EVALSAN by the company JAN DEKKER.

(7) The polymers corresponding to the general formula (XI) are described for example in French Patent 1,400,366, the disclosure of which is incorporated by reference:

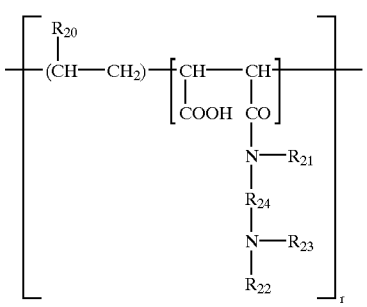
(XI)

in which: $R_{20}$ is chosen from a hydrogen atom, a $CH_3O$, $CH_3CH_2O$ radical, and a phenyl radical; $R_{21}$ is hydrogen and a lower alkyl radical, such as methyl or ethyl; $R_{22}$ is chosen from a hydrogen and a lower alkyl radical, such as methyl or ethyl; $R_{23}$ is chosen from a lower alkyl radical, such as methyl or ethyl or a radical corresponding to the formula: $—R_{24}—N(R_{22})_2$; $R_{24}$ is chosen from a $—CH_2—CH_2—$ group, a $—CH_2—CH_2—CH_2—$ group, and a $—CH_2—CH(CH_3)—$ group; $R_{22}$ having the meanings mentioned above, as well as the higher homologues of these radicals and containing up to 6 carbon atoms.

(8) Amphoteric polymers of the —D—X—D—X— type chosen from:

a) the polymers obtained by the action of chloroacetic acid or sodium chloroacetate on the compounds containing at least one unit of formula (XII):

—D—X—D—X—D— (XII)

where D is a radical

and X is the symbol E or E', E or E', which are identical or different, are a bivalent radical which is an alkylene radical with a linear or branched chain containing up to 7 carbon atoms in the principal chain, which is unsubstituted or substituted with hydroxyl groups and which may contain, in addition, oxygen, nitrogen or sulphur atoms, 1 to 3 aromatic and/or heterocyclic rings. The oxygen, nitrogen and sulphur atoms being present in the form of ether, thioether, sulphoxide, sulphone, sulphonium, alkylamine or alkenylamine groups, or hydroxyl, benzylamine, amine oxide, quaternary ammonium, amide, imide, alcohol, ester and/or urethane groups.

b) The polymers of formula:

$$—D—X—D—X— \quad (XII')$$

where D is a radical

and X is the symbol E or E' and, at least once, E'. E having the meaning indicated above and E' is a bivalent radical which is an alkylene radical with a linear or branched chain having up to 7 carbon atoms in the principal chain, which is unsubstituted or substituted with at least one hydroxy radical and containing at least one nitrogen atoms. The nitrogen atom is substituted with an alkyl chain optionally interrupted by an oxygen atom and necessarily containing at least one carboxyl functional group or at least one hydroxyl functional group and betainized by reaction with chloroacetic acid or sodium chloroacetate.

(9) The copolymers ($C_1$–$C_5$)alkyl vinyl ether/maleic anhydride partially modified by semiamidation with an N,N-dialkylaminoalkylamine, such as N,N-dimethylaminopropylamine or by semiesterification with an N,N-dialkanolamine. These copolymers may also contain other vinyl comonomers, such as vinylcaprolactam.

The amphoteric film-forming polymers particularly preferred according to the invention are those of the family (3) such as the copolymers whose CTFA name is Octylacrylamide/acrylates/butylaminoethylmethacrylate copolymer, such as the products sold under the names AMPHOMER, AMHOMER LV 71 or LOVOCRYL 47 by the company NATIONAL STARCH and those of the family (4) such as the methyl methacrylate/dimethylcarboxymethylammonioethyl methacrylate copolymers, for example sold under the name DIAFORMER Z301 by the company SANDOZ.

The nonionic film-forming polymers which can be used according to the present invention are chosen for example from:

vinylpyrrolidone homopolymers;

vinylpyrrolidone and vinyl acetate copolymers;

polyalkyloxazolines such as the polyethyl-oxazolines offered by the company DOW CHEMICAL under the names PEOX 50,000, PEOX 200,000 and PEOX 500,000;

vinyl acetate homopolymers, such as the product offered under the name APPRETAN EM by the company HOECHST or the product offered under the name RHODOPAS A 012 by the company RHONE POULENC;

acrylic ester and vinyl acetate copolymers, such as the product offered under the name RHODOPAS AD 310 from RHONE POULENC;

ethylene and vinyl acetate copolymers, such as the product offered under the name APPRETAN TV by the company HOECHST;

copolymers of vinyl acetate and maleic ester, for example dibutyl maleate, such as the product offered under the name APPRETAN MB EXTRA by the company HOECHST;

maleic anhydride and polyethylene copolymers;

homopolymers of alkyl acrylates and the homopolymers of alkyl methacrylates, such as the product offered under the name MICROPEARL RQ 750 by the company MATSUMOTO or the product offered under the name LUHYDRAN A 848 S by the company BASF;

copolymers of acrylic esters, such as for example the copolymers of alkyl acrylates and alkyl methacrylates, such as the products offered by the company ROHM & HAAS under the names PRIMAL AC-261 K and EUDRAGIT NE 30 D, by the company BASF under the names ACRONAL 601, LUHYDRAN LR 8833 or 8845, by the company HOECHST under the names APPRETAN N 9213 or N9212;

copolymers of acrylonitrile and of a nonionic monomer chosen for example from butadiene and alkyl (meth) acrylates. There may be mentioned the products offered under the names NIPOL LX 531 B by the company NIPPON ZEON or those offered under the name CJ 0601 B by the company ROHM & HMS;

polyurethanes, such as the products offered under the names ACRYSOL RM 1020 and ACRYSOL RM 2020 by the company ROHM & HAAS, the products URAFLEX XP 401 UZ, URAFLEX XP 402 UZ by the company DSM RESINS;

copolymers of alkyl acrylate and urethane, such as the product 8538-33 by the company NATIONAL STARCH;

polyamides, such as the product ESTAPOR LO 11 offered by the company RHONE POULENC; and chemically modified or unmodified nonionic guar gums.

The unmodified nonionic guar gums are for example the products sold under the name VIDOGUM GH 175 by the company UNIPECTINE and under the name JAGUAR C by the company MEYHALL.

The modified nonionic guar gums which can be used according to the invention are preferably modified with ($C_1$–$C_6$) hydroxyalkyl groups. There may be mentioned, by way of example, hydroxymethyl, hydroxyethyl, hydroxypropyl and hydroxybutyl groups.

These guar gums are well known in the state of the art and may, for example, be prepared by reacting corresponding alkene oxides, such as for example propylene oxides, with the guar gum so as to obtain a guar gum modified with hydroxypropyl groups.

Such nonionic guar gums optionally modified with hydroxyalkyl groups are for example sold under the trade names JAGUAR HP8, JAGUAR HP60 and JAGUAR HP120, JAGUAR DC 293 and JAGUAR HP 105 by the company MEYHALL, or under the name GALACTASOL 4H4FD2 by the company AQUALON.

The alkyl radicals of the nonionic polymers have from 1 to 6 carbon atoms unless otherwise stated.

According to the invention, it is also possible to use the film-forming polymers of the graft siliconized type comprising a polysiloxane portion and a portion comprising a nonsiliconized organic chain, one of the two portions constituting the principal chain of the polymer, the other being grafted on the principal chain. These polymers are, for example, described in Patent Applications EP-A-0,412,704, EP-A-0,412,707,EP-A-0,640,105 and WO 95/00578, EP-A-0,582,152 and WO 93/23009 and in U.S. Pat. Nos. 4,693,935, 4,728,571 and 4,972,037, the disclosures of all of which are incorporated by reference. These polymers are preferably anionic or nonionic.

Such polymers are for example the copolymers which may be obtained by free-radical polymerization from the mixture of monomers comprising:

a) 50 to 90% by weight of tert-butyl acrylate;

b) 0 to 40% by weight of acrylic acid;

c) 5 to 40% by weight of siliconized macromer of formula (XIII):

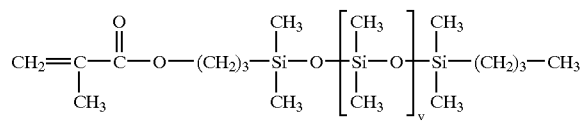

(XIII)

with v being an integer ranging from 5 to 700; the percentages by weight being calculated relative to the total weight of the monomers.

Other examples of graft siliconized polymers are in particular polydimethylsiloxanes (PDMS) onto which there are grafted, via a connecting chain of thiopropylene type, mixed polymer units of the poly(meth)acrylic acid type and of the alkyl poly(meth)acrylate type and polydimethylsiloxanes (PDMS) onto which there are grafted, via a connecting chain of the thiopropylene type, polymer units of the isobutyl poly(meth)acrylate type.

It is also possible to use, as film-forming polymers, polyurethanes which are functionalized or otherwise, or siliconized or otherwise.

The polyurethanes which are particularly targeted by the present invention are those described in Patents EP 0,751,162, EP 0,637,600, FR 2,743,297 and EP 0,648,485, by the company L'Oréal, as well as Patents EP 0,656,021 or WO 94/03510 by the company BASF and EP 0,619,111 by the company National Starch, the disclosures of all of which are incorporated by reference.

According to the invention, the fixing and/or conditioning polymer(s) are present in the composition in an amount ranging from 0.001% to 20% by weight, preferably from 0.01% to 10% by weight and more particularly from 0.1 to 3% by weight relative to the total weight of the final composition.

The compositions of the invention also advantageously contain at least one surfactant which is generally present in an amount ranging from 0.1% to 60% by weight approximately, preferably from 3% to 40% and still more preferably from 5% to 30%, relative to the total weight of the composition.

This surfactant can be chosen from anionic, amphoteric and nonionic surfactants, or mixtures thereof.

The surfactants which are suitable for carrying out the present invention are especially the following:

(i) Anionic Surfactant(s):

Their nature is not of truly critical importance within the context of the present invention.

Thus, by way of example of anionic surfactants that can be employed, by themselves or as mixtures, in the context of the present invention, there may be mentioned especially (nonlimiting list) the salts (in particular alkali metal, especially sodium, salts, ammonium salts, amine salts, amino alcohol salts or magnesium salts) of the following compounds: alkyl sulphates, alkyl ether sulphates, alkylamido ether sulphates, alkylarylpolyether sulphates, monoglyceride sulphates, alkyl sulphonates, alkyl phosphates, alkylamidesulphonates, alkyl aryl sulphonates, a-olefinsulphonates, paraffin-sulphonates, alkyl sulphosuccinates, alkyl ether sulphosuccinates, alkylamidesulphosuccinates, alkyl sulphosuccinamates, alkyl sulphoacetates, alkyl ether phosphates, acyl sarcosinates, acyl isethionates and N-acyltaurates, the alkyl or acyl radical of all these different compounds preferably containing from 8 to 24 carbon atoms, and the aryl radical preferably denoting a phenyl or benzyl group. Among the anionic surfactants which are further usable there may also be mentioned the salts of fatty acids such as the salts of oleic, ricinoleic, palmitic and stearic acids, the acids of copra oil or of hydrogenated copra oil, and acyl lactylates in which the acyl radical contains 8 to 20 carbon atoms. It is also possible to employ weakly anionic surfactants, like alkyl-D-galactosideuronic acids and salts thereof, as well as the polyoxyalkylenated carboxylic $(C_6–C_{24})$alkyl ether acids, the polyoxyalkylenated carboxylic $(C_6–C_{24})$alkylaryl ether acids, the polyoxyalkylenated carboxylic $(C_6–C_{24})$alkyl amidoether acids and their salts, in particular those containing from 2 to 50 ethylene oxide groups and mixtures thereof.

Among the anionic surfactants, the use of the salts of alkyl sulphates and of alkyl ether sulphates and mixtures thereof is preferred according to the invention.

(ii) Nonionic Surfactant(s):

The nonionic surfactants themselves are also compounds which are well known per se (in this respect see especially the "Handbook of Surfactants" by M. R. Porter, published by Blackie & Son (Glasgow and London), 1991, pp. 116–178, the disclosure of which is incorporated by reference) and, in the context of the present invention, their nature is not of critical importance. They can thus be chosen especially from (nonlimiting list) alcohols, alphadiols, alkylphenols or polyethoxylated, polypropoxylated or polyglycerolated fatty acids which have a fatty chain containing, for example, 8 to 18 carbon atoms, it being possible for the number of ethylene oxide or propylene oxide groups to range especially from 2 to 50 and it being possible for the number of glycerol groups to range especially from 2 to 30. The copolymers of ethylene oxide and propylene oxide and the condensates of ethylene oxide and propylene oxide with fatty alcohols may also be mentioned; the polyethoxylated fatty amides preferably containing from 2 to 30 mol of ethylene oxide, the polyglycerolated fatty amides on average containing 1 to 5 glycerol groups and in particular 1.5 to 4, the polyethoxylated fatty amines preferably containing 2 to 30 mol of ethylene oxide, the oxyethylenated fatty acid esters of sorbitan containing from 2 to 30 mol of ethylene oxide, the fatty acid esters of sucrose, the fatty acid esters of polyethylene glycol, alkylpolyglycosides, the N-alkylglucamine derivatives, amine oxides such as the oxides of $(C_{10}–C_{14})$ alkylamines or the N-acylaminopropylmorpholine oxides. It will be noted that alkylpolyglycosides constitute nonionic surfactants which are particularly well suited within the context of the present invention.

(iii) Amphoteric Surfactant(s):

The amphoteric surfactants, the nature of which is not of critical importance in the context of the present invention, may be especially (nonlimiting list) derivatives of aliphatic secondary or tertiary amines in which the aliphatic radical is a linear or branched chain containing 8 to 22 carbon atoms and containing at least one water-solubilizing anionic group (for example carboxylate, sulphonate, sulphate, phosphate or phosphonate); $(C_8–C_{20})$alkylbetaines, sulphobetaines, $(C_8–C_{20})$alkylamido$(C_1–C_6)$alkylbetaines or $(C_8–C_{20})$alkylamido$(C_1–C_6)$alkylsulphobetaines may further be mentioned.

Among the amine derivatives there may be mentioned the products sold under the name MIRANOL, as described in U.S. Pat. Nos. 2,528,378 and 2,781,354, the disclosures of which are incorporated by reference, and of structures:

$$R_2\text{—CONHCH}_2\text{CH}_2\text{—N}(R_3)(R_4)(\text{CH}_2\text{COO—}) \qquad (2)$$

in which: $R_2$ is an alkyl, preferably an alkyl radical of an acid $R_2$—COOH present in hydrolysed coprah oil, or a heptyl, nonyl or undecyl radical, $R_3$ is a beta-hydroxyethyl group and $R_4$ is a carboxymethyl group; and

$$R_5\text{—CONHCH}_2\text{CH}_2\text{—N(B)(C)} \qquad (3)$$

in which:

B is —$CH_2CH_2OX'$, C is —$(CH_2)_z$—Y', with z being 1 or 2,

X' is a —$CH_2CH_2$—COOH group or a hydrogen atom,

Y' is —COOH or a radical —$CH_2$—CHOH—$SO_3H$, $R_5$ is an alkyl, preferably, an alkyl radical of an acid $R_5$—COOH present in coprah oil or in hydrolysed linseed oil, or a $C_7$, $C_8$, $C_{11}$ or $C_{13}$ alkyl radical, or a $C_{17}$ alkyl radical and its iso form, or an unsaturated $C_{17}$ radical.

These compounds are classified in the CTFA dictionary, 5th edition, 1993, the disclosure of which is incorporated by reference, under the names Disodium Cocoamphodiacetate, Disodium Lauroamphodiacetate, Disodium Caprylamphodiacetate, Disodium Caprylamphodiacetate, Disodium Cocoamphodipropionate, Disodium Lauroamphodipropionate, Disodium Caprylamphodipropionate, Disodium Caprylamphodipropionate, Lauroamphodipropionic acid, Cocoamphodipropionic acid.

By way of example, there may be mentioned the cocoamphodiacetate marketed under the trade name MIRANOL C2M concentrate by the company RHONE POULENC.

In the compositions in accordance with the invention, there are preferably used mixtures of surfactants and in particular mixtures of anionic surfactants and mixtures of anionic surfactants and of amphoteric or nonionic surfactants. A particularly preferred mixture is a mixture comprising at least one anionic surfactant and at least one amphoteric surfactant.

An anionic surfactant is preferably used which is chosen from sodium, triethanolamine or ammonium $(C_{12}–C_{14})$alkyl sulphates, oxyethylenated sodium, triethanolamine or ammonium $(C_{12}–C_{14})$alkyl ether sulphates containing 2.2 mol of ethylene oxide, sodium cocoyl isethionate and sodium $(C_{14}–C_{16})$alphaolefin sulphonate and their mixtures with:

either an amphoteric surfactant, such as the amine derivatives called disodium cocoamphodipropionate or sodium cocoamphopropionate marketed in particular by the company RHONE POULENC under the trade name MIRANOL C2M CONC in aqueous solution at 38% of active material and under the name MIRANOL C32;

or an amphoteric surfactant of the zwitterionic type, such as the alkylbetaines in particular cocobetaine marketed under the name DEHYTON AB 30 in aqueous solution at 32% AM by the company HENKEL.

The composition of the invention may also contain at least one additive chosen from thickeners, perfumes, pearlescent agents, preservatives, sunscreens which are siliconized or otherwise, vitamins, waxes, compounds of the ceramide type, polymers other than those of the invention, proteins, protein hydrolysates, fatty acids containing a linear or branched $(C_{16}–C_{40})$ chain, such as 18-methyleicosanoic acid, fatty acid esters, fatty alcohols, hydroxy acids, vitamins, panthenol, cationic surfactants, mineral, vegetable, animal or synthetic oils and any other additive which is conventionally used in the cosmetic field and which does not substantially adversely affect the properties of the compositions according to the invention.

These additives are present in the composition according to the invention in proportions which can range from 0 to 20% by weight relative to the total weight of the composition. The precise amount of each additive is easily determined by persons skilled in the art according to its nature and its function.

The compositions in accordance with the invention can be more particularly used for washing or treating keratinous materials such as the hair, the skin, the eyelashes, the eyebrows, the nails, the lips, the scalp and more particularly the hair.

In particular, the compositions according to the invention are detergent compositions such as shampoos, shower gels and foam baths. In this embodiment of the invention, the compositions comprise a generally aqueous washing base.

The surfactant(s) forming the washing base may equally well be chosen, alone or as mixtures, from anionic, amphoteric, nonionic and cationic surfactants as defined above.

The quantity and the quality of the washing base are those sufficient to confer on the final composition a satisfactory foaming and/or detergent power.

Thus, according to the invention, the washing base can be present in the composition in an amount ranging from 4% to 50% by weight, preferably from 6% to 35% by weight, and still more preferably from 8% to 25% by weight, of the total weight of the final composition.

The subject of the invention is also a method of treating keratinous materials, such as the skin or the hair, comprising applying to the keratinous materials a cosmetic composition as defined above, and then in optionally carrying out a rinsing with water.

Thus, this method according to the invention allows the retention of the hairstyle, the treatment, the care or the washing of or the removal of make-up from the skin, the hair or any other keratinous material.

The compositions of the invention may also be provided in the form of a hair conditioner to be rinsed off or otherwise, of compositions for permanent waving, hair straightening, dyeing or bleaching, or alternatively in the form of rinse-off compositions to be applied before or after dyeing, bleaching, permanent waving or hair straightening or alternatively between the two stages of a permanent waving or a hair straightening treatment.

The compositions of the invention may also be provided in the form of cleansing compositions for the skin, and in particular in the form of bath or shower solutions or gels or of make-up removing products.

The compositions according to the invention may also be provided in the form of aqueous or aqueous-alcoholic lotions for skin and/or hair care.

The cosmetic compositions according to the invention may be provided in the form of a gel, a milk, a cream, an emulsion, a thickened lotion or a foam and may be used for the skin, the nails, the eyelashes, the lips and more particularly the hair.

The compositions may be packaged in various forms, in particular in vaporizers, pump dispensers or in aerosol containers in order to allow application of the composition in vaporized form or in foam form. Such forms of packaging are advisable, for example, when it is desired to obtain a spray, a lacquer or a foam for treating the hair.

In the text which follows or in the preceding text, the percentages expressed are by weight.

The invention will now be illustrated more fully with the aid of the following examples which should not be considered as limiting it to the embodiments described. In the examples, AS means active substance.

EXAMPLE 1

A shampoo having the following composition was prepared

| | |
|---|---|
| Sodium lauryl ether sulphate (2.2 EO) | 8 g AS |
| Sodium N-cocoylamidoethyl N-ethoxy-carboxymethyl glycinate (MIRANOL C2M CONC NP from RHODIA CHIMIE) | 4 g AS |
| Methacrylic acid/acrylic acid/ethyl acrylate/methyl methacrylate copolymer as an aqueous dispersion containing 25% of AS (AMERHOLD DR 25 from AMERCHOL) | 0.5 g AS |
| Terpolymer of methacrylamidopropyltrimethyl-ammonium chloride, acrylic acid and stearyl methacrylate (49/49/2 mol %) | 1 g AS |
| Preservative | qs |
| pH adjusted to 7 | 7 |
| Water qs | 100 g |

Hair washed with the shampoo according to the invention was soft, sleek and was easily shaped.

EXAMPLE 2

A shampoo having the following composition was prepared

| | |
|---|---|
| Sodium N-cocoylamidoethyl N-ethoxy-carboxymethyl glycinate (MIRANOL C2M CONC NP from RHODIA CHIMIE) | 8 g AS |
| Sodium lauryl ether carboxylate containing 4.5 mol of ethylene oxide (AKYPOSOFT 45NV from KAO) | 5 g AS |
| Polyurethane-1 (INCI name) in aqueous-alcoholic solution containing 30% of active substance neutralized with AMP (LUVISET PUR from BASF) | 1.2 g AS |
| Terpolymer of methacrylamidopropyltrimethyl-ammonium chloride, acrylic acid and stearyl methacrylate (49/49/2 mol %) | 0.5 g AS |
| Sodium chloride | 2 g |
| Preservative | qs |
| pH adjusted to 7 (citric acid or sodium hydroxide) | 7 |
| Water qs | 100 g |

What is claimed is:

1. A cosmetic composition comprising at least one fixing and/or conditioning polymer and at least one amphoteric polymer comprising from 1 to 20 mol % of at least one monomeric unit chosen from (meth)acrylate and (meth)acrylamide having at least one fatty chain, the fatty chain having from 8 to 30 carbon atoms, wherein the at least one fixing and/or conditioning polymer and the at least one amphoteric polymer are not the same polymer.

2. The composition according to claim 1, wherein the composition further comprises a cosmetically acceptable medium.

3. The composition according to claim 1, wherein the at least one amphoteric polymer comprises from 1.5 to 15 mol % of monomeric units comprising a fatty chain relative to the total number of moles of monomeric units in said at least one polymer.

4. The composition according to claim 3, wherein the at least one amphoteric polymer comprises from 1.5 to 6 mol % of monomeric units comprising a fatty chain relative to the total number of moles of monomeric units in said at least one polymer.

5. The composition according to claim 1, wherein the at least one amphoteric polymer results from copolymerization 1) of at least one monomer chosen from (meth)acrylate and (meth)acrylamide of formula (Ia) and (Ib):

$$R_1-CH=C(R_2)-C(=O)-Z-(C_nH_{2n})-N^+(R_3)(R_4)R_5 \quad A^- \quad (Ia)$$

$$R_1-CH=C(R_2)-C(=O)-Z-(C_nH_{2n})-N(R_3)(R_4) \quad (Ib)$$

in which: $R_1$ and $R_2$, which are identical or different, are a hydrogen atom or a methyl radical; $R_3$ $R_4$ and $R_5$, which are identical or different, are chosen from linear and branched alkyl radicals having from 1 to 30 carbon atoms;

Z is an NH group or an oxygen atom;

n is an integer ranging from 2 to 5; and $A^-$ is an anion derived from an organic or inorganic acid, 2) of at least one monomer chosen from (meth)acrylate and (meth)acrylamide of formula (II)

$$R_6-CH=CR_7-COOH \quad (II)$$

in which: $R_6$ and $R_7$, which are identical or different, are a hydrogen atom or a methyl radical; and 3) of at least one monomer chosen from (meth)acrylate and (meth)acrylamide of formula (III):

$$R_6-CH=CR_7-COXR_8 \quad (III)$$

in which: $R_6$ and $R_7$, which are identical or different, are a hydrogen atom or a methyl radical; X is an oxygen or nitrogen atom; and $R_8$ is chosen from linear and branched alkyl radicals having from 1 to 30 carbon atoms;

wherein at least one of the (meth)acrylate and (meth) acrylamide monomers of formula (Ia), (Ib) or (III)

comprise at least one fatty chain having from 8 to 30 carbon atoms.

6. The composition according to claim 5, wherein the at least one monomer of formula (Ia) and (Ib) is chosen from:
dimethylaminoethyl methacrylate, dimethylamino-ethyl acrylate, and
diethylaminoethyl methacrylate, diethylaminoethyl acrylate,
dimethylaminopropyl methacrylate, dimethylaminopropyl acrylate, and
dimethylaminopropylmethacrylamide, dimethylaminopropylacrylamide, these monomers being optionally quaternized.

7. The composition according to claim 5, wherein the at least one monomer of formula (Ia) is chosen from acrylamidopropyltrimethyl-ammonium chloride and methacrylamidopropyltrimethyl-ammonium chloride.

8. The composition according to claim 5, wherein the at least one monomer of formula (II) is chosen from acrylic acid, methacrylic acid, crotonic acid and 2-methylcrotonic acid.

9. The composition according to claim 5, wherein the at least one monomer of formula (III) is chosen from ($C_{12}$–$C_{22}$) alkyl acrylates and methacrylates.

10. The composition according to claim 9, wherein the at least one monomer of formula (III) is chosen from ($C_{16}$–$C_{18}$) alkyl acrylates and methacrylates.

11. The composition according to claim 1, wherein the at least one amphoteric polymer is chosen from acrylic acid/acrylamidopropyltrimethylammonium chloride/stearyl methacrylate copolymers.

12. The composition according to claim 1, wherein the at least one amphoteric polymer is present in the composition in an amount ranging from 0.05 to 10% by weight relative to the total weight of the composition.

13. The composition according to claim 1, wherein the at least one fixing polymer is an anionic polymer chosen from:
polymers containing carboxyl units derived from unsaturated mono- or dicarboxylic acid monomers of formula (IX):

in which: n is an integer ranging from 0 to 10; A is a methylene group, optionally linked to the carbon atom of the unsaturated group or to the neighboring methylene group, when n is greater than 1, through a heteroatom; $R_7$ is chosen from a hydrogen atom, a phenyl group, and a benzyl group; $R_8$ is chosen from a hydrogen atom, a carboxyl group, and a lower alkyl group; $R_9$ is chosen from a hydrogen atom, a lower alkyl group, a —$CH_2$—COOH group, a phenyl group, and a benzyl group; and
polymers comprising units derived from sulphonic acid.

14. The composition according to claim 13, wherein the heteroatom is oxygen or sulphur.

15. The composition according to claim 13, wherein the units derived from sulphonic acid are chosen from vinylsulphonic, styrenesulphonic, and acrylamidoalkylsulphonic units.

16. The composition according to claim 13, wherein the anionic polymer is chosen from:

acrylic acid copolymers;
copolymers derived from crotonic acid;
polymers derived from itaconic, fumaric acids, maleic acids or anhydrides with vinyl esters, vinyl ethers, vinyl halides, phenylvinyl derivatives, acrylic acid and its esters;
copolymers of methacrylic acid and of methyl methacrylate;
copolymers of methacrylic acid and of ethyl acrylate;
copolymers of vinyl acetate/crotonic acid; and
terpolymers of vinyl acetate/crotonic acid/-polyethylene glycol.

17. The composition according to claim 16, wherein the acrylic acid copolymers are terpolymers of acrylic acid/ethyl acrylate/N-tert-butylacrylamide.

18. The composition according to claim 16, wherein the copolymers derived from crotonic acid are terpolymers of vinyl acetate/vinyl tert-butyl-benzoate/crotonic acid and terpolymers of crotonic acid/vinyl acetate/vinyl neododecanoate.

19. The composition according to claim 16, wherein the polymers derived from itaconic, fumaric acids, maleic acids or anhydrides with vinyl esters, vinyl ethers, vinyl halides, phenylvinyl derivatives, acrylic acid and its esters are chosen from monoesterified maleic anhydride/methylvinyl ether copolymers.

20. The composition according to claim 1, wherein the at least one fixing and/or conditioning polymer is an amphoteric polymer chosen from polymers containing units which are derived from:
a) at least one monomer chosen from acrylamides and methacrylamides substituted on the nitrogen by an alkyl radical,
b) at least one acidic comonomer containing at least one reactive carboxyl group, and
c) at least one basic comonomer.

21. The composition according to claim 20, wherein the at least one basic comonomer is chosen from esters with primary, secondary, tertiary and quaternary amine substituents of acrylic and methacrylic acids and the products of quaternization of dimethylaminoethyl methacrylate with dimethyl or diethyl sulphate.

22. The composition according to claim 1, wherein the at least one fixing and/or conditioning polymer is a nonionic polymer chosen from:
polyalkyloxazolines;
vinyl acetate homopolymers;
acrylic ester and vinyl acetate copolymers;
ethylene and vinyl acetate copolymers;
copolymers of vinyl acetate and maleic ester;
maleic anhydride and polyethylene copolymers;
homopolymers of alkyl acrylates and the homopolymers of alkyl methacrylates;
copolymers of acrylic esters;
copolymers of acrylonitrile and of a nonionic monomeric unit chosen from butadiene and alkyl (meth)acrylates; and
copolymers of alkyl acrylate and urethane.

23. The composition according to claim 22, wherein the copolymers of acrylic esters are copolymers of alkyl acrylates and alkyl methacrylates.

24. The composition according to claim 1, wherein the at least one fixing and/or conditioning polymer is chosen from cationic polymers which contain units comprising primary, secondary, tertiary and/or quaternary amine groups which may either form part of the principal polymer chain, or which may be carried by a side substituent directly linked thereto.

25. The composition according to claim 24, wherein the cationic polymers are chosen from quaternary cellulose ether derivatives, cationic cyclopolymers, cationic polysaccharides, and quaternary polymers of vinylpyrrolidone and vinylimidazole.

26. The composition according to claim 25, wherein the cationic cyclopolymers are chosen from homopolymers of diallyldimethylammonium chloride and copolymers of diallyldimethylammonium chloride and of acrylamide.

27. The composition according to claim 25, wherein the quaternary cellulose ether derivatives are chosen from hydroxyethylcelluloses which have reacted with an epoxide substituted with a trimethylammonium group.

28. The composition according to claim 25, wherein the cationic polysaccharides are chosen from guar gums modified with a 2,3-epoxypropyltrimethylammonium salt.

29. The composition according to claim 1, wherein the at least one fixing and/or conditioning polymer is present in the composition at a concentration ranging from 0.001% to 20% by weight relative to the total weight of the composition.

30. The composition according to claim 29, wherein the at least one fixing and/or conditioning polymer is present in the composition at a concentration ranging from 0.01% to 10% by weight relative to the total weight of the composition.

31. The composition according to claim 1, wherein the composition also comprises at least one surfactant chosen from anionic, nonionic, and amphoteric surfactants.

32. The composition according to claim 31, wherein the at least one surfactant is present in the composition in a concentration ranging from 0.1% to 60% by weight relative to the total weight of the composition.

33. The composition according to claim 32, wherein the at least one surfactant is present in the composition in a concentration ranging from 3.0% to 40% by weight relative to the total weight of the composition.

34. The composition according to claim 33, wherein the at least one surfactant is present in the composition in a concentration ranging from 5.0% to 30% by weight relative to the total weight of the composition.

35. A shampoo, a conditioner, a permanent waving composition for hair, a straightening composition for hair, a dyeing composition for hair, a bleaching composition for hair, a rinse-out composition to be applied between two stages of a permanent waving or hair straightening treatment, or a cleansing composition for the skin comprising at least one fixing and/or conditioning polymer and at least one amphoteric polymer comprising from 1 to 20 mol % of at least one monomeric unit chosen from (meth)acrylate and (meth)acrylamide having at least one fatty chain, the fatty chain having from 8 to 30 carbon atoms wherein the at least one fixing and/or conditioning polymer and the at least one amphoteric polymer are not the same polymer.

36. A method for washing or caring for a keratinous material comprising applying at least one fixing and/or conditioning polymer and at least one amphoteric polymer comprising from 1 to 20 mol % of at least one monomeric unit chosen from (meth)acrylate and (meth)acrylamide having at least one fatty chain, the fatty chain having from 8 to 30 carbon atoms wherein the at least one fixing and/or conditioning polymer and the at least one amphoteric polymer are not the same polymer.

37. A process for treating a keratinous material, comprising
   applying to the keratinous material a cosmetic composition comprising at least one fixing and/or conditioning polymer and at least one amphoteric polymer comprising from 1 to 20 mol % of at least one monomeric unit chosen from (meth)acrylate and (meth)acrylamide having at least one fatty chain, the fatty chain having from 8 to 30 carbon atoms wherein the at least one fixing and/or conditioning polymer and the at least one amphoteric polymer are not the same polymer, and then optionally rinsing with water.

38. The method of claim 37, wherein the keratinous material is hair.

39. A method of making a cosmetic composition comprising including in said composition at least one fixing and/or conditioning polymer and at least one amphoteric polymer comprising from 1 to 20 mol % of at least one monomeric unit chosen from (meth)acrylate and (meth)acrylamide having at least one fatty chain, the fatty chain having from 8 to 30 carbon atoms wherein the at least one fixing and/or conditioning polymer and the at least one amphoteric polymer are not the same polymer.

40. A method for increasing the fixing and/or conditioning effect of a composition comprising at least one fixing and/or conditioning polymer by including in said composition at least one amphoteric polymer comprising from 1 to 20 mol % of at least one monomeric unit chosen from (meth)acrylate and (meth)acrylamide having at least one fatty chain, the fatty chain having from 8 to 30 carbon atoms wherein the at least one fixing and/or conditioning polymer and the at least one amphoteric polymer are not the same polymer.

* * * * *